United States Patent [19]

Katz et al.

[11] 4,298,736

[45] Nov. 3, 1981

[54] CARBON-CAFFEINE SEPARATION

[75] Inventors: Saul N. Katz, Monsey; George E. Proscia, West Sayville, both of N.Y.

[73] Assignee: General Foods Corporation, White Plains, N.Y.

[21] Appl. No.: 159,724

[22] Filed: Jun. 16, 1980

[51] Int. Cl.$^3$ ............................................ C07D 473/12
[52] U.S. Cl. .................................... 544/274; 544/275
[58] Field of Search ........................ 544/274, 275, 273

[56] References Cited

U.S. PATENT DOCUMENTS 1,855,026  10/1980  Livingstone et al. ................ 544/274
2,508,545  5/1950   Shuman ............................... 544/274

Primary Examiner—Nicholas S. Rizzo
Attorney, Agent, or Firm—Thomas V. Sullivan; Bruno P. Struzzi; Thomas R. Savoie

[57] ABSTRACT

The object of the invention is to provide an improved process for recovering caffeine adsorbed on activated carbon.

Caffeine removed from the commercial decaffeination of vegetable materials and extracts can be effectively removed from the extraction solvent, or can be purified, by the use of activated carbon. Unfortunately, the caffeine is tenaciously held by the carbon and none of the techniques currently available for removing the caffeine is wholly satisfactory.

The recovery of caffeine from activated carbon is accomplished according to the present invention by employing a liquid, food-grade caffeine solvent which comprises an organic acid or alcohol, and which is capable of competing for the active sites on the carbon occupied by the caffeine to displace at least a portion of the caffeine which is then dissolved in the solvent. After the desired period of contact, the caffeine is separated from the solvent. The solvent will preferably comprise glacial acetic acid or an acetic acid azeotrope, and contact will preferably be at a temperature above 100° C.

12 Claims, No Drawings

CARBON-CAFFEINE SEPARATION

TECHNICAL FIELD

The present invention relates to decaffeination, and particularly to an improved process for recovering caffeine from an activated carbon adsorbent.

The decaffeination of vegetable materials and vegetable material extracts is of major commercial importance. Also significant is the recovery and sale of the caffeine removed from vegetable sources such as coffee and tea. It is known that activated carbon is a good adsorbent in caffeine recovery and purification procedures, but the carbon tends to hold the caffeine so tenaciously that, often, significant quantities of caffeine are lost or reduced in commercial value. None of the techniques currently available to the art for separating the caffeine from the carbon has been wholly satisfactory in terms of both degree and quality of caffeine recovery.

BACKGROUND ART

The recovery of caffeine from decaffeinating solvents has been an active area of concern for many years. For example, in U.S. Pat. No. 2,508,545, Shuman discloses that activated carbon and other adsorbents had been used to remove impurities from solutions of caffeine extracted from coffee. Shuman indicates that until the time of his invention caffeine losses due to adsorption onto the carbon ran as high as 10 to 14%. To rectify this, Shuman disclosed alternate use of organic and aqueous extractions with the final aqueous extraction being done at a pH of at least 7. While activated carbon is employed to remove impurities from the aqueous extract, the amounts employed are apparently small and no mention of separating caffeine from the carbon is made. Similarly, in U.S. Pat. No. 2,472,881, Bender employs activated carbon to remove impurities from an aqueous caffeine solution but does not discuss the steps taken to recover the caffeine adsorbed on the carbon.

Recently, an improved decaffeination method was disclosed in U.S. Pat. No. 3,879,569 wherein quantitative extraction of caffeine from raw coffee beans is achieved with moist supercritical carbon dioxide. This process produces an extract from which essentially all of the caffeine can be removed by activated carbon. Unfortunately, the prior art techniques do not economically provide good levels of recovery of caffeine or they require the use of chlorinated hydrocarbon solvents which are otherwise avoided by the use of carbon dioxide as an extractant.

DISCLOSURE OF INVENTION

The present invention now enables improved recovery of caffeine from an activated carbon adsorbent, by an improved process which comprises: contacting activated carbon having caffeine adsorbed thereon with a liquid, food-grade caffeine solvent which comprises an organic acid or an alcohol, and which is capable of displacing at least a portion of the caffeine from active sites on the carbon; maintaining the contact for a period of time and at a temperature effective for the solvent to displace at least a portion of the caffeine from the carbon and dissolve the displaced caffeine; and separating the caffeine from the solvent.

The present invention takes advantage of the discovery that some liquid, food-grade caffeine solvents which have the ability to effect desorption both by their strong solvent ability and their ability to displace the adsorbed material from active sites on the adsorbent, are extremely effective in separating caffeine from carbon adsorbents. The strong solvent effect causes a partitioning between the activated carbon and the solvent. The site displacement effect is achieved by the solvent molecules themselves competing for the active adsorbent sites. Once a caffeine molecule is displaced, it is then taken into solution by the solvent which is a strong solvent for caffeine.

The solvents employed according to the present invention are employed in their liquid state and preferably at temperatures in excess of 100° C. to obtain the greatest rates of recovery. Temperature has a strong effect on desorption and should therefore be as high as possible, consistent with maintaining the solvent as a liquid. Where temperatures higher than the boiling point of the solvent are desired, it will be necessary to employ pressures in excess of atmospheric. It is preferred, however, to maintain the pressure at no greater than about atmospheric. Therefore, the higher boiling solvents are preferred.

Because the caffeine is valuable for food and pharmaceutical use, the solvents must be food-grade. By this, it is meant that the materials are on the Generally Recognized As Safe (GRAS) list maintained by the Food and Drug Administration to this type of use. This is important because where any measurable quantity of a non-GRAS material works its way into either the product caffeine or the product tea or coffee, the value of the product will be seriously diminished, if not wholly lost.

The organic acids and alcohols which are food-grade, liquid at the proposed processing temperature and preferably at room temperature, excellent solvents for caffeine, and capable of displacing caffeine from the active sites on the carbon, are effective solvents for use according to the invention. Preferably, the solvent will comprise a member selected from the group consisting of acetic acid, propionic acid, butyric acid, ethanol, isopropanol, benzyl alcohol, butanol, amyl alcohol, and azeotropes comprising at least one of these. Among the co-solvents which can be employed in forming the azeotropes are water, n-hexane, n-heptane, n-octane, toluene, benzyl acetate, methylene chloride, ethyl acetate and other food-grade solvents. The preferred solvents are those which have boiling points over 100° C., and of these glacial acetic acid and acetic acid azeotropes are the most preferred. The azeotropes of acetic acid with butyl alcohol, iso-amyl alcohol, toluene, and n-octane all have boiling points above 100° C. as can be seen from the following table:

| Acetic Acid Azeotropes | Boiling Point (°C.) |
| --- | --- |
| Acetic Acid 43% wt. Butyl Alcohol 57% wt. | 120.3 |
| Acetic Acid 16% wt. Iso-Amyl Alcohol 84% wt. | 133.0 |
| Acetic Acid 65% wt. Toluene 35% wt. | 105.4 |
| Acetic Acid 53% wt. n-Octane 47% wt. | 105.0 |

Other azeotropes suitable for use in the process of the invention, but requiring the use of superatmospheric pressures when temperatures of 100° C. or more are employed, are:

| Acetic Acid Azeotropes | Boiling Point (°C.) |
| --- | --- |
| Acetic Acid 6% wt. n-Hexane 94% wt. | 68 |
| Acetic Acid 33% wt. n-Heptane 67% wt. | 95 |
| Other Azeotropes | |
| Ethanol 96% wt. Water 4% wt. | 78.2 |
| Isopropanol 88% wt. Water 12% wt. | 80.1 |
| Benzyl Alcohol 9% wt. Water 91% wt. | 99.9 |
| Non-Azeotropes | |
| Ethyl Acetate 10–50% wt. Acetic Acid 50–90% wt. | Non-Azeotropic |
| Methylene Chloride 10–50% wt. Acetic Acid 50–90% wt. | Non-Azeotropic |
| Benzyl Acetate 10–30% wt. Acetic Acid 70–90% wt. | Non-Azeotropic |

Based on economy, effect on final product quality and effectiveness, glacial acetic acid is the most preferred of all the solvents.

The solvent is maintained in contact with the carbon having caffeine adsorbed thereon for a period of time and at a temperature effective for the solvent to displace at least a portion of the caffeine from the carbon and dissolve the displaced caffeine. As noted above, preferred temperatures will be above 100° C., but the specific temperature for any particular process will be selected on its own set of economic considerations and may be below this. Practical contact times will be determined on the basis of the desired degree of recovery and the desorption rate for a particular system. Preferably, the contact time should be sufficient to permit displacement of at least 75% by weight of the caffeine from the carbon and into solution with the solvent. Because the caffeine is valuable as a product and, if not removed from the carbon, decreases the adsorbent capacity of the carbon, still higher rates of displacement, on the order of 90% by weight or more, are desired.

As the activated carbon adsorbent can be any of those types commercially available which are effective caffeine adsorbents and capable of withstanding the rigors of recycling permitted by the invention. Preferred activated carbons are those prepared from coconut, coal and lignite, particularly those available commercially from Calgon Corporation, ICI, Carborundum and Union Carbide Corporation.

After contact for the requisite period of time, the activated carbon is preferably separated from the solvent prior to separation of the caffeine from the solvent. The simplest and most effective manner for removing the carbon from the solvent is by filtration.

The caffeine can be separated from the solvent in any suitable manner such as steam distillation or simply evaporating the solvent. In a preferred form of recovery, steam is passed through the caffeine-containing solvent in a vented vessel until the solvent concentration is reduced to about zero, most preferably about <1 ppm, leaving an aqueous caffeine solution. The caffeine is then precipitated from the aqueous solution by cooling to form pure white needle-shaped crystals.

BEST MODE FOR CARRYING OUT THE INVENTION

The following examples are for the purpose of illustrating and explaining the best mode for carrying out the invention, but are not meant to be limiting in any regard. Unless otherwise indicated, all parts and percentages are by weight.

EXAMPLE 1

One hundred parts of glacial acetic acid and 10 parts of activated carbon pellets containing 10% by weight caffeine, obtained from the process of U.S. Pat. No. 3,879,569, were admixed and then refluxed in a vessel at atmospheric pressure and 117° C. for two hours. The acetic acid was decanted from the carbon and found to contain 0.801% caffeine. The carbon had 9.5 parts of acetic acid remaining on it. The caffeine was recovered from the solution by evaporation. The total amount of caffeine in the acetic acid was 0.725 parts, nearly 73% recovery in a single stage.

EXAMPLE 2

The procedure of Example 1 was repeated but this time the components were introduced into a Soxhlet extraction tube and refluxed at 117° C. for four hours. Total recovery of caffeine based on the 10% initial caffeine was 99%.

EXAMPLE 3

The procedure of Example 2 was repeated, but this time employing a solvent containing 57 parts of n-butyl alcohol and 43 parts of glacial acetic acid. After four hours contact at 120° C., 82% of the caffeine was recovered. On evaporation, white crystals of caffeine precipitated from the solution.

EXAMPLE 4

In this example, green coffee beans are contacted with methylene chloride solvent to obtain a caffeine extract as described in U.S. Pat. No. 3,671,263. The solvent is removed from the extract by evaporation, leaving a brown, crude caffeine sludge containing large amounts of impurities in addition to caffeine. The sludge is preliminarily dissolved in water. Then the caffeine extract is contacted with DARCO powdered activated carbon which adsorbs most of the impurities from the extract to prepare it for crystallization into pure, white caffeine crystals. The carbon picks up about 10% caffeine in addition to the impurities. The caffeine is removed from the carbon by contacting the charcoal with glacial acetic acid for 4 hours at 100° C. in a vessel. The carbon is separated from the acetic acid solution by filtration and the acid is evaporated to leave relatively pure crystals of caffeine. The acetic acid is condensed and recycled. The carbon is regenerated for recycle by thermal reactivation.

The above description has been for the purpose of teaching a person skilled in the art how to practice the invention. It is not intended to describe in detail each and every modification and variation of the invention which will become apparent to those skilled in the art upon study. It is applicant's intention, however, that all such modifications and variations be included within the scope of the invention as defined by the following claims.

What is claimed is:

1. A process for recovering caffeine from activated carbon comprising:
   contacting activated carbon having caffeine adsorbed thereon with a liquid, food-grade caffeine solvent which comprises an organic acid or an alcohol, and which is capable of displacing at least a portion of the caffeine from active sites on the carbon;

maintaining the contact for a period of time and at a temperature effective for the solvent to displace at least a portion of the caffeine from the carbon and dissolve the displaced caffeine; and separating caffeine from the solvent.

2. A process according to claim 1 wherein the solvent comprises a member selected from the group consisting of acetic acid, propionic acid, butyric acid, ethanol, isopropanol, benzyl alcohol, butanol, amyl alcohol, and azeotropes comprising at least one of these.

3. A process according to claim 2 wherein the contact is maintained at a temperature of at least 100° C.

4. A process according to claim 3 wherein the contact is maintained at a pressure in excess of atmospheric.

5. A process according to claim 3 wherein the contact is maintained at a pressure of no greater than about atmospheric.

6. A process according to claim 2 wherein the solvent is glacial acetic acid or an acetic acid azeotrope containing a co-solvent selected from the group consisting of butyl alcohol, iso-amyl alcohol, toluene, n-hexane, n-heptane, and n-octane.

7. A process according to either of claims 2 or 6 wherein the solvent is glacial acetic acid or an acetic acid azeotrope containing a co-solvent selected from the group consisting of butyl alcohol, iso-amyl alcohol, toluene, and n-octane.

8. A process according to either of claims 1 or 6 wherein the solvent is glacial acetic acid.

9. A process according to claim 1 wherein contact is maintained for a period of time sufficient to permit displacement of at least 75% by weight of the caffeine from the carbon and into solution with the solvent.

10. A process according to claim 9 wherein the solvent is separated from the carbon by filtration prior to separating the caffeine from the solvent.

11. A process according to claim 10 wherein the caffeine is separated from the solvent by steam distillation.

12. A process according to claim 10 wherein the caffeine is separated from the solvent by evaporating the solvent.

* * * * *